US007594751B2

(12) United States Patent
Grebner et al.

(10) Patent No.: US 7,594,751 B2
(45) Date of Patent: Sep. 29, 2009

(54) BIPLANE X-RAY SYSTEM

(75) Inventors: Albert Grebner, Eckental (DE); Klaus Klingenbeck-Regn, Nürnberg (DE); Winfried Lurz, Fürth (DE); Stefan Sattler, Forchheim (DE); Manfred Schönborn, Gerhardshofen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/218,359

(22) Filed: Jul. 15, 2008

(65) Prior Publication Data

US 2009/0028290 A1 Jan. 29, 2009

(30) Foreign Application Priority Data

Jul. 19, 2007 (DE) ...................... 10 2007 033 716

(51) Int. Cl.
*H05G 1/02* (2006.01)

(52) U.S. Cl. ...................................... 378/197; 378/196

(58) Field of Classification Search .......... 378/193–198
See application file for complete search history.

(56) References Cited

U.S. PATENT DOCUMENTS

| | | | | |
|---|---|---|---|---|
| 5,515,416 | A * | 5/1996 | Siczek et al. | 378/197 |
| 5,923,721 | A * | 7/1999 | Duschka | 378/92 |
| 6,104,780 | A * | 8/2000 | Hanover et al. | 378/92 |
| 2003/0091152 | A1* | 5/2003 | Dietz et al. | 378/197 |
| 2007/0003014 | A1* | 1/2007 | Boese et al. | 378/95 |
| 2008/0247506 | A1 | 10/2008 | Maschke | 378/15 |

FOREIGN PATENT DOCUMENTS

| | | |
|---|---|---|
| DE | 102006061178 A1 | 6/2008 |

* cited by examiner

*Primary Examiner*—Courtney Thomas

(57) ABSTRACT

In a biplane X-ray system, a robot is used for moving at least a pair comprising an X-ray radiation source and an X-ray detector. The robot can be a buckling arm robot bearing an X-ray C-arm. It is also possible for the X-ray radiation source and X-ray detector each to be suspended from the ceiling of the room by means of robot arms.

14 Claims, 4 Drawing Sheets

23 23 24 10 12 14 18 16 26 22 30 28 20

BIPLANE X-RAY SYSTEM

CROSS REFERENCE TO RELATED APPLICATIONS

This application claims priority of German application No. 10 2007 033 716.9 filed Jul. 19, 2007, which is incorporated by reference herein in its entirety.

FIELD OF THE INVENTION

The invention relates to a biplane X-ray system. Biplane X-ray systems of this kind are known with two X-ray imaging devices each comprising an X-ray radiation source, an X-ray detector and means for moving the X-ray radiation source and X-ray detector.

BACKGROUND OF THE INVENTION

Until now, X-ray C-arms have been used with both X-ray imaging devices. The first X-ray imaging device is usually a conventional floor-based X-ray C-arm system and the second X-ray imaging device comprises a stand suspended from the ceiling with a pivotable X-ray C-arm. The ceiling stand is movable so that the first X-ray imaging device can also be used alone, that is as a monoplane system.

When using a biplane X-ray system, two image planes are defined corresponding to the name of the system. Usually, beforehand, the relative position of the two image planes to each other is defined, for example a tilting angle, which is usually around 90°, and this relative position is subsequently maintained. This means that the X-ray radiation source and X-ray detector of the first X-ray imaging device have to be moved in coordination with the X-ray radiation source and X-ray detector of the second X-ray imaging device. The mechanics of the X-ray C-arm system on the one hand and the fact that the second X-ray C-arm is arranged on a ceiling stand result in restricted movement options. This means that it is not possible to record all image combinations. With the previous systems, for example, it is not possible to change the so-called isocenter of the X-ray C-arm. It is not possible to travel along scanning paths which satisfy a so-called completeness condition. A completeness condition provides information on whether the total number of all the images recorded enables a complete analysis or not.

SUMMARY OF THE INVENTION

It is the object of the invention to expand the possibilities of biplane X-ray systems and hereby in particular to overcome the drawbacks mentioned above.

The object is achieved by the fact that the means for moving at least one of the X-ray imaging devices comprise at least one robot.

The use of robots was considered earlier in connection with monoplane systems. For example, DE 102006061178.0, which was published after the filing data of the present application, discloses the use of a 6-axis buckling arm robot on which an X-ray C-arm is arranged.

The present invention now also uses robots with biplane X-ray systems. The use of robots, such as, for example, (6-axis) buckling arm robots, provides greatly increased flexibility in the possible movements. There are more degrees of freedom, for example the isocenter is now also variable with biplane X-ray systems so that inter alia the working height is adjustable.

In a particularly simple embodiment, using the above-described conventional biplane X-ray system as a basis, a floor-standing robot is now used with the first X-ray imaging device, while the second X-ray imaging device remains unchanged, that is it comprises an X-ray C-arm stand which is suspended from the ceiling and preferably movable.

This embodiment combines in a particularly economic way a monoplane system with robots, such as is already under development, with the X-ray C-arm stand, which does not need to be further developed.

In another preferred embodiment, robots are provided for both X-ray imaging devices, and, to be precise, both robots can stand on the floor, both robots can be suspended from the ceiling or one robot can stand on the floor and the other robot can be suspended from the ceiling.

It is also possible to use a conventional buckling arm robot as the robot suspended from the ceiling.

However, for special adaptation to the spatial conditions, the X-ray imaging device arranged on the ceiling can also comprise a first robot arm to which the X-ray radiation source is attached and a second robot arm to which the X-ray detector is attached. Dispensing with an X-ray C-arm enables additional flexibility to be obtained. The robot arms can in particular, for example, be embodied with the provision of a suitable joint so that they permit the folding upward of the X-ray radiation source and X-ray detector in the direction of ceiling (or onto the ceiling). The use of the two separate robot arms also makes it possible to embody them so they can move relative to each other. The rotation of the whole entity is not excluded. On the contrary, it is possible for the robot arms to be suspended from a rotatable plate. The plate can also be tiltable so that an additional degree of freedom is obtained which is not known with conventional stands with an X-ray C-arm. The X-ray radiation source and X-ray detector can also each be tiltable on their robot arm, in particular by the provision of a suitable joint at the respective end of the robot arms.

The means for controlling the movements of the robot arms or the movements at the robot arms should obviously be embodied so that the X-ray detector always receives the radiation emitted by the X-ray radiation source, that is a movement should take place in a coupled manner.

All the aforementioned embodiments, in which both X-ray imaging devices have a robot, have the advantage that they then do not necessarily have to work together within a biplane X-ray system. On the contrary, it is conceivable for the two X-ray imaging devices to be used simultaneously independently of each other as monoplane systems. In the case of conventional biplane X-ray systems, only one of the X-ray imaging devices, namely usually the floor-standing X-ray C-arm system can be used as a monoplane system, while the X-ray C-arm stand is merely moved away and cannot be used separately.

Particularly high flexibility is obtained with the embodiment with robots, to which an X-ray C-arm is attached, if said arm can be removed. The robots can then also be used for other tasks. For example, it can be provided that the X-ray radiation source can be attached to one robot and the X-ray detector to the other robot and these two robots can then be moved in coordination. In this way, a particularly highly flexible monoplane system can be provided on the basis of the two robots provided for the biplane X-ray system.

It can also be provided that one of the robots retains the X-ray C-arm and that the second robot is coupled to a patient table unit for moving the patient table. The robots can then be moved in coordination and the additional degrees of freedom in comparison to a conventional monoplane system, which are associated with the mobility of the patient table, can result in completely new possibilities for the utilization of the system.

The aforementioned methods for the use of the possibilities provided by a biplane X-ray system means the procurement of a biplane X-ray system of this kind will be particularly rewarding.

BRIEF DESCRIPTION OF THE DRAWINGS

The following describes preferred embodiments of the invention with reference to the drawings, which show FIG. 1 a biplane X-ray system according to a first embodiment of the invention, FIG. 2 a biplane X-ray system according to a second embodiment of the invention, FIG. 3 a biplane X-ray system according to a third embodiment of the invention and FIG. 4 an X-ray imaging device for a further embodiment of the invention.

DETAILED DESCRIPTION OF THE INVENTION

Figure 1:
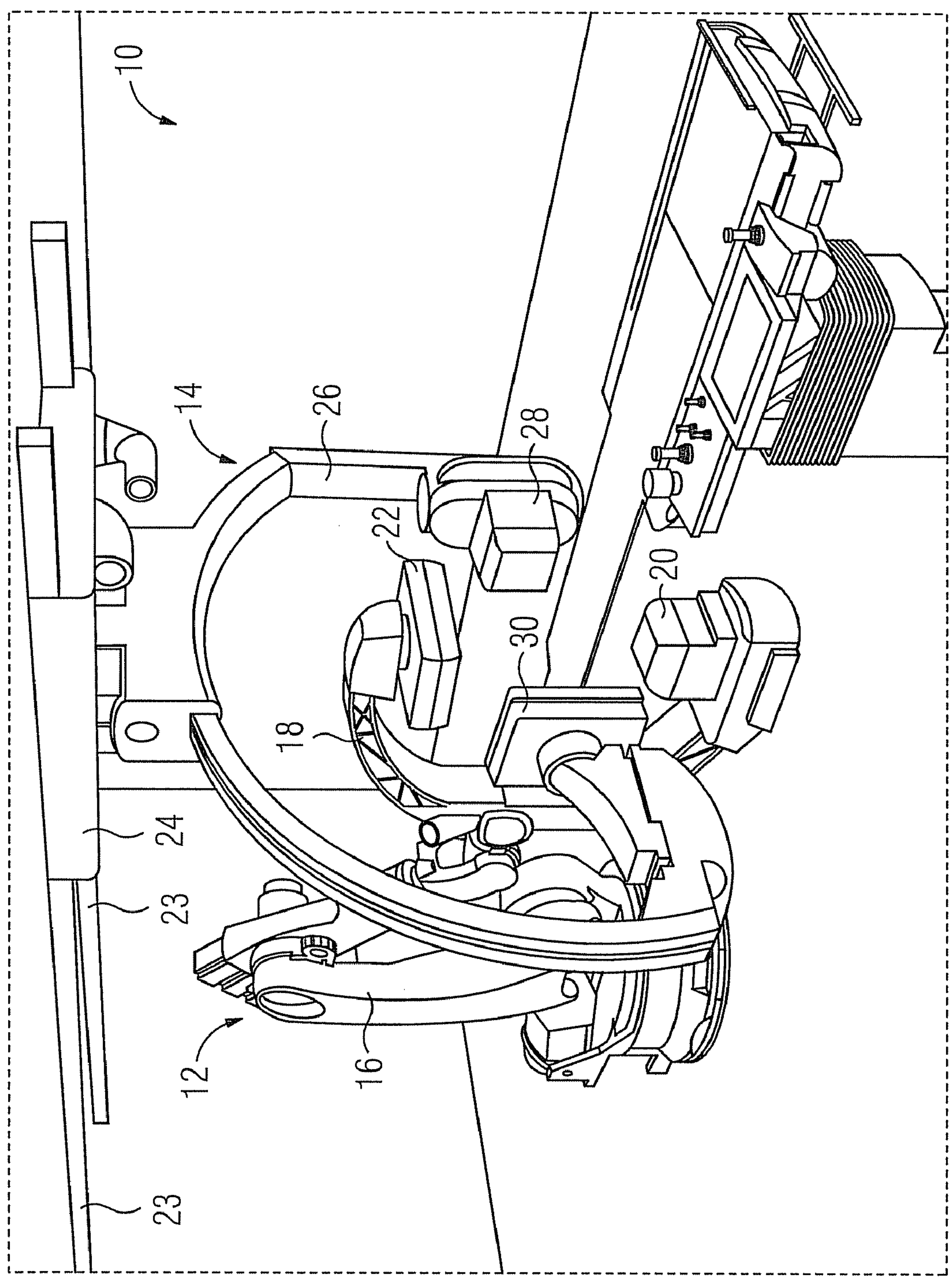

A biplane X-ray system shown in FIG. 1, designated 10 overall, comprises a first X-ray imaging device 12 and a second X-ray imaging device 14. The first X-ray imaging device 12 comprises a 6-axis buckling arm robot 16, to which is attached a C-arm 18, which bears an X-ray source 20 and an X-ray detector 22. The second X-ray imaging device 14 is a conventional X-ray imaging device comprising a stand 24 which can be moved on rails 23 supporting a movable X-ray C-arm 26 to which an X-ray radiation source 28 and an X-ray detector 30 are also attached. The biplane X-ray system 10 differs from conventional biplane X-ray systems in the use of the robot 16. The robot 16 has many more degrees of freedom than a conventional X-ray C-arm system. This makes certain positions of the X-ray radiation source 20 and X-ray detector 22 possible, in particular also relative to the X-ray radiation source 28 and the X-ray detector 30, therefore, the imaging possibilities of the biplane X-ray system 10 are expanded compared to conventional biplane X-ray systems.

Figure 2:
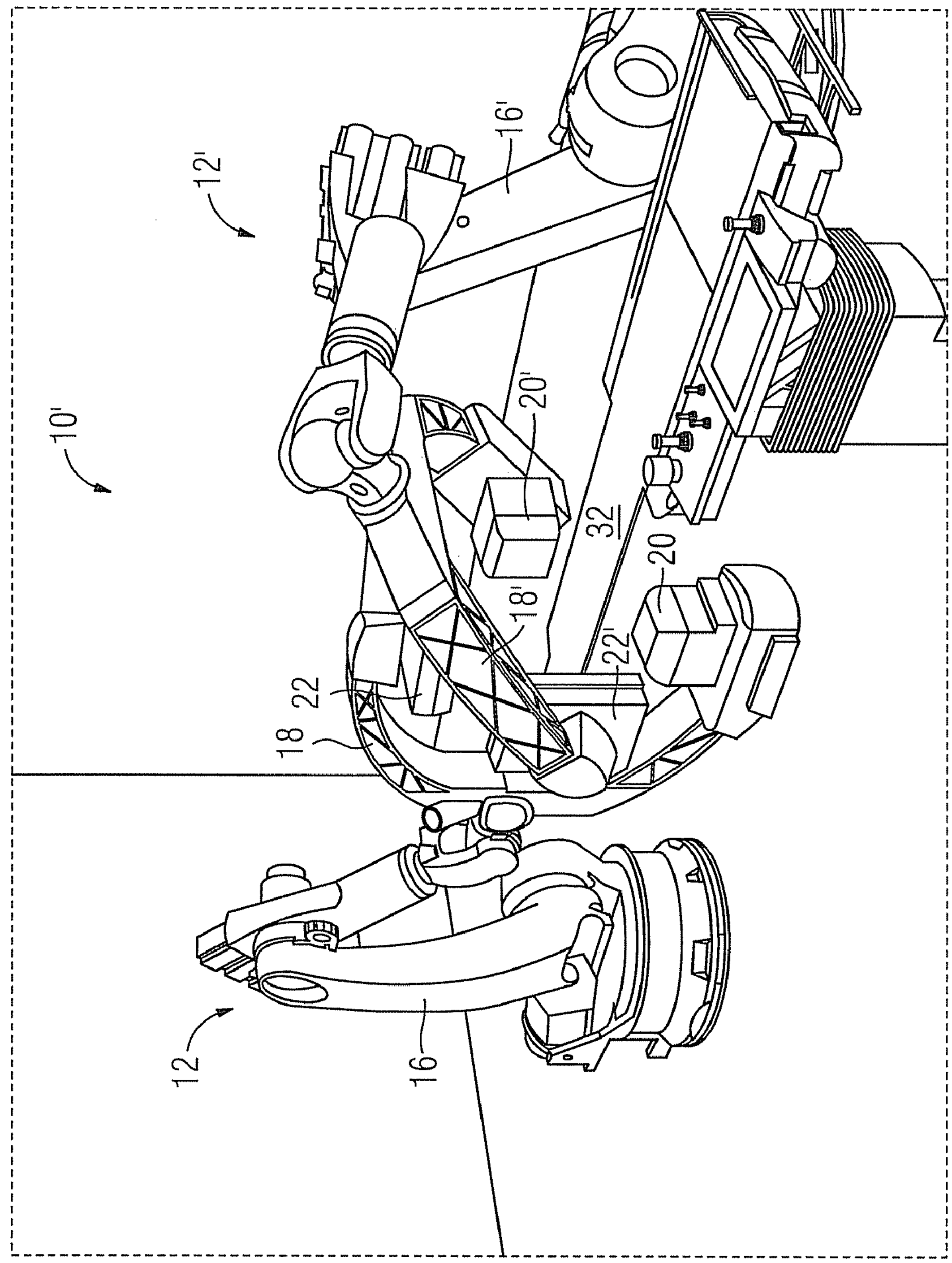

FIG. 2 shows a second embodiment of the invention. The biplane X-ray system 10' shown there comprises the first X-ray imaging device 12 with the robot 16, which has the first biplane X-ray system 10 in any case, and, as a second X-ray imaging device, an identically designed X-ray imaging device 12' with a robot 16', a C-arm 18', an X-ray radiation source 20' and an X-ray detector 22'. The use of two robots 16 and 16' means that, compared to the biplane X-ray system 10, the movement possibilities are further increased with the biplane X-ray system 10', image scanning can be performed satisfying the completeness condition, and to be precise, in a relatively shorter time which saves on contrast medium. The two X-ray imaging devices 12 and 12' can also be used independently of each other. While FIG. 2 only shows one patient table 32, it can be provided that the first X-ray imaging device 12 is assigned to this patient table 32 and the second X-ray imaging device 12' is turned by a large angle of around 180° and so is assigned to a further patient table not shown in FIG. 2. The two X-ray imaging devices 12 and 12' of the biplane X-ray system 10' can therefore be used individually as monoplane X-ray systems.

Figure 3:
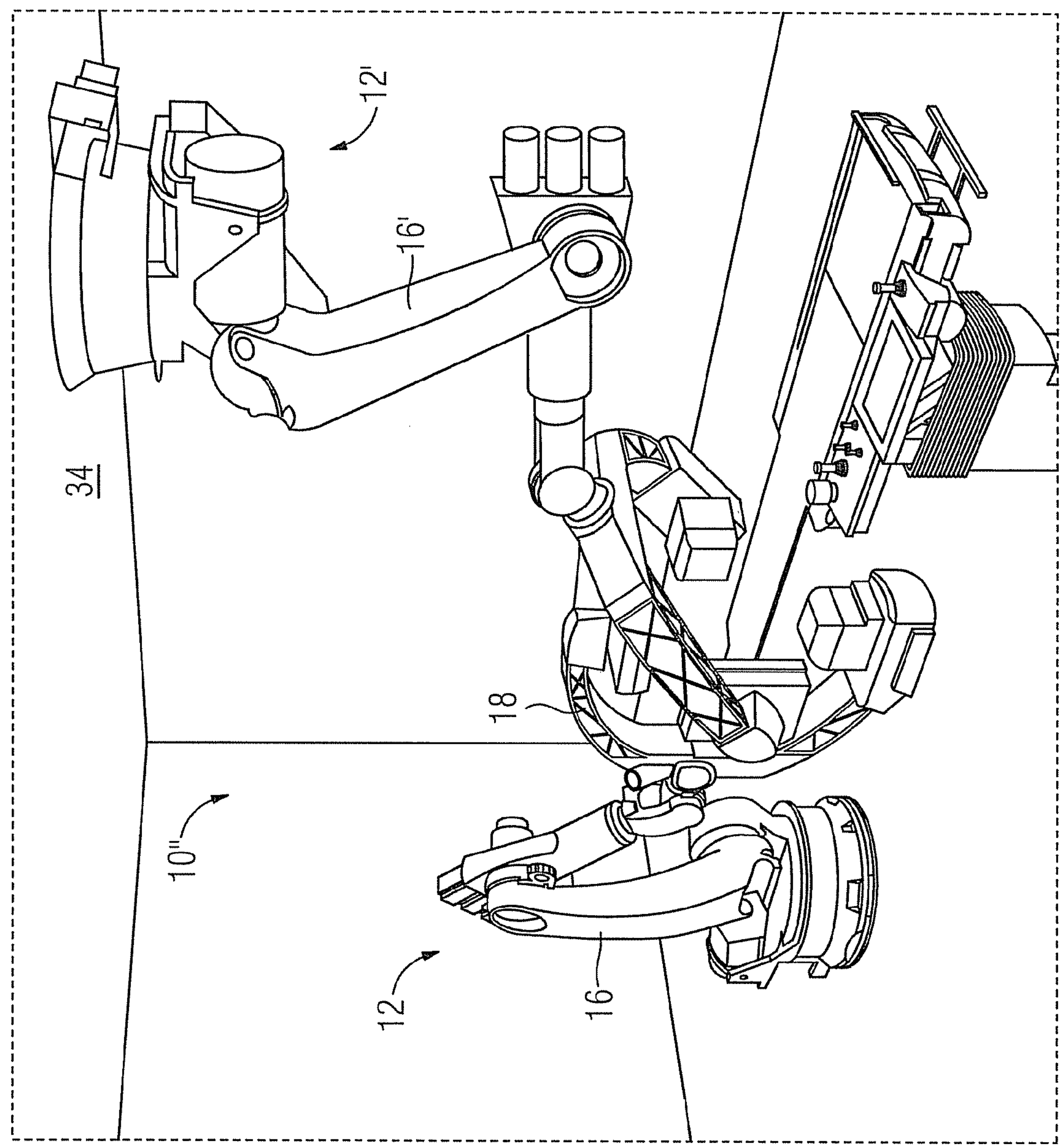

In a variation of the embodiment according to FIG. 2, in which the robots 16 and 16' are standing on the floor, FIG. 3 shows a biplane X-ray system 10", in which the second X-ray imaging device 12' is attached to the ceiling of the room 34. The attachment of the robot 16' to the ceiling of the room 34 permits the simple buckling away of the robot 16' in the direction of ceiling 34, so that the robot 16' does not disturb the operation of the first X-ray imaging device 12 when this is used as a monoplane X-ray device. The attachment of the X-ray imaging device 12' to the ceiling of the room 34 does not exclude the possibility of this second X-ray imaging device 12' being used simultaneously with the first X-ray imaging device 12 as a monoplane X-ray system.

Figure 4:
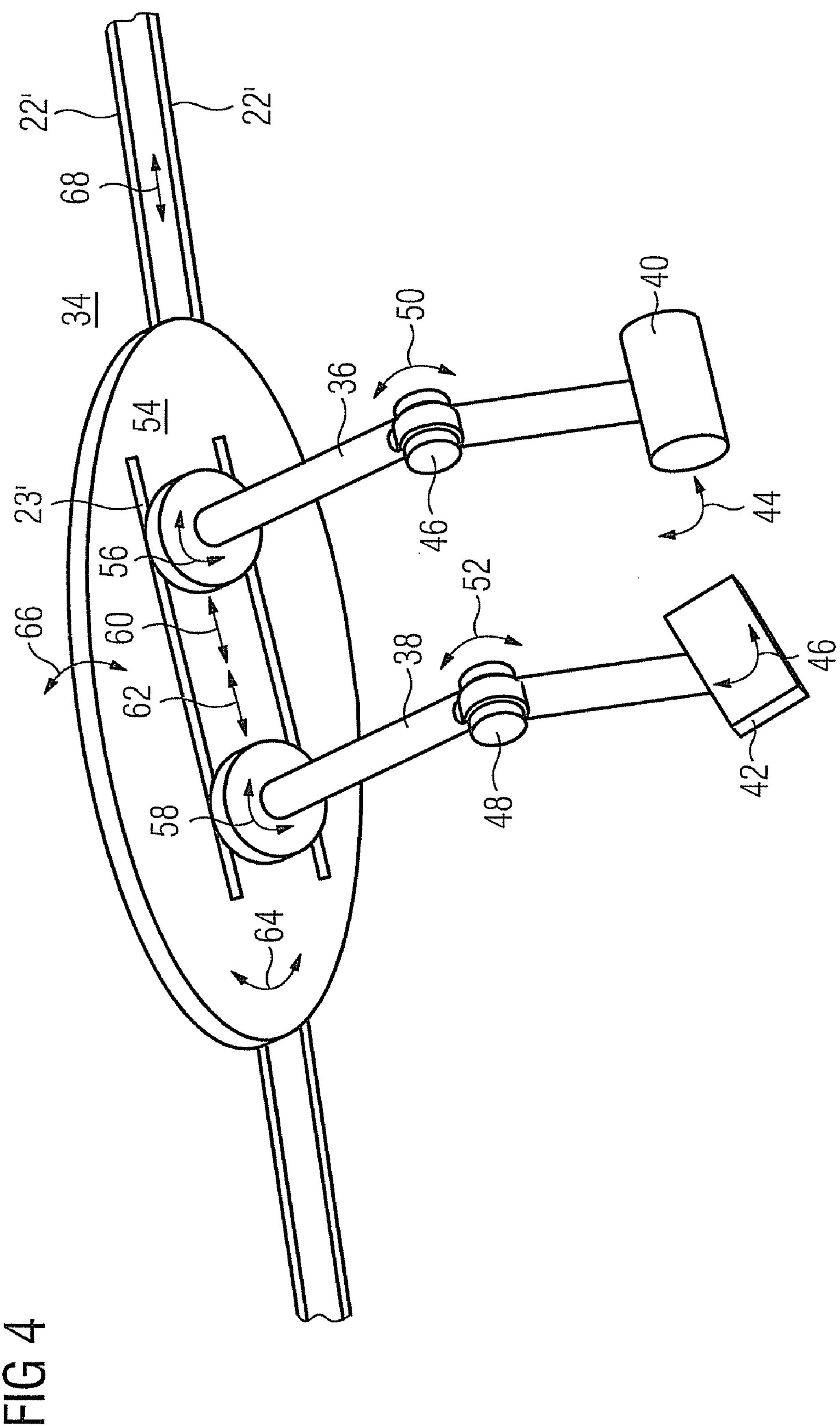

It not absolutely necessary to use a single buckling arm robot which bears the C-arm with the X-ray radiation source and the X-ray detector. It is conceivable for two individual robot arms 36 and 38 to be used. This is shown in FIG. 4: in particular with the system attached to the ceiling, the X-ray radiation source 40 is attached to the first robot arm 36 and the second X-ray radiation source 42 is attached to the second robot arm 38. The robot arms 36 and 38 permit a plurality of movements. The X-ray radiation source 40 and the X-ray detector 42 should on the one hand be attached to the robot arms 36 and 38 in such a way that they may be moved (tilted) back and forth as indicated by the arrows 44 and 46 relative to the robot arms 36 and 38.

Provided approximately in the center of the robot arms are joints 46, 48 which enable the robot arm 36 or 38 to be folded back as indicated by the arrows 50 and 52. The X-ray radiation source 40 and the X-ray detector 42 can, therefore, be folded in the direction of the ceiling of the room 34. If the second X-ray imaging device stands, like the X-ray imaging device 12, on the floor, the robot arms 36 and 38 do not impede said device when it works as a monoplane X-ray system.

The X-ray arms 36 and 38 are suspended from a base plate 54, and to be precise, can be rotated as indicated by the arrows 56 and 58. Provided on the base plate 54 are rails 23 which enable a relative movement of the robot arms 36 and 38 toward or away from each other as indicated by the arrows 60 and 62. The base plate 54 is also rotatable (see arrow 64) and is characterized by the property of being tiltable as indicated by the arrow 66 so that a degree of freedom is obtained which conventional X-ray imaging devices like the X-ray imaging device 14 do not have when they are suspended from the ceiling of the room 34.

Moreover, the base plate 54 can also be moved as a whole in rails 23" as indicated by the arrow 68 along the ceiling of the room 34.

Means for controlling the diverse movements should be designed so that the movements of the X-ray tube 40 and X-ray detector 42 take place in coordination with each other when biplane images are desired.

The invention claimed is:

1. A biplane X-ray system, comprising:

a first X-ray imaging device;

a first X-ray radiation source arranged on the first X-ray imaging device;

a first X-ray detector arranged on the first X-ray imaging device;

a first robot that moves the first X-ray radiation source and the first X-ray detector;

a second X-ray imaging device;

a second X-ray radiation source arranged on the second X-ray imaging device;

a second X-ray detector arranged on the second X-ray imaging device; and a second device that moves the second X-ray radiation source and the second X-ray detector, wherein the second device comprises a second robot, and wherein the first and the second imaging devices each comprises an X-ray C-arm detachably attached to the first and the second robots respectively.

2. The biplane X-ray system as claimed in claim 1, wherein the first robot is a buckling arm robot.

3. The biplane X-ray system as claimed in claim 1, wherein the first robot comprises a robot standing on a floor and the second device comprises an X-ray C-arm stand suspended from a ceiling.

4. The biplane X-ray system as claimed in claim 1, wherein the second robot is a buckling arm robot.

5. The biplane X-ray system as claimed in claim 1, wherein the first and the second robots each comprises a robot standing on a floor.

6. The biplane X-ray system as claimed in claim 1, wherein the first and the second robots are suspended from a ceiling.

7. The biplane X-ray system as claimed in claim 1, wherein the first robot comprises a robot standing on a floor and the second robot is suspended from a ceiling.

8. The biplane X-ray system as claimed in claim 7, wherein the second robot comprises a first robot arm for attaching the second X-ray radiation source and a second robot arm for attaching the second X-ray detector.

9. The biplane X-ray system as claimed in claim 8, wherein the first and the second robot arms fold the second X-ray radiation source and the second X-ray detector to a ceiling.

10. The biplane X-ray system as claimed in claim 8, wherein the first and the second robot arms moves relative to each other.

11. The biplane X-ray system as claimed in claim 8, wherein the first and the second robot arms are suspended from a plate that is rotatable or tiltable.

12. The biplane X-ray system as claimed in claim 8, wherein the second X-ray radiation source or the second X-ray detector is rotatable or tiltable.

13. A method for operating a biplane X-ray system, comprising:

detachably attaching a first X-ray C-arm of the biplane X-ray system to a first robot;

detachably attaching a second X-ray C-arm of the biplane X-ray system to a second robot;

removing the first X-ray C-arm from the first robot;

removing the second X-ray C-arm from the second robot;

attaching an X-ray radiation source on the first robot;

attaching an X-ray detector on the second robot; and moving the first and the second robots coordinately.

14. A method for operating a biplane X-ray system, comprising:

detachably attaching a first X-ray C-arm of the biplane X-ray system to a first robot;

detachably attaching a second X-ray C-arm of the biplane X-ray system to a second robot;

removing the first X-ray C-arm from the first robot;

attaching a patient table on the first robot; and moving the first and the second.

* * * * *